United States Patent [19]

Tsuru et al.

[11] Patent Number: 4,865,733

[45] Date of Patent: Sep. 12, 1989

[54] CELL SEPARATOR DEVICE

[75] Inventors: Sumiaki Tsuru, Tokyo; Shoichi Mori; Noriko Komatsu, both of Ooimachi; Shigeo Fujii, Kawagoe, all of Japan

[73] Assignees: Toa Nenryo Kogyo K.K.; Asahi Kogaku Kogyo Kabushiki Kaisha, both of Tokyo, Japan

[21] Appl. No.: 28,571

[22] Filed: Mar. 20, 1987

[30] Foreign Application Priority Data

Mar. 22, 1986 [JP] Japan .................................. 61-064518

[51] Int. Cl.⁴ ............................................. B01D 39/06
[52] U.S. Cl. .................................. 210/266; 210/502.1; 210/505; 210/509; 210/510.1
[58] Field of Search ....................... 210/679, 689–691, 210/263, 266, 502.1, 505, 508, 509, 510.1

[56] References Cited

U.S. PATENT DOCUMENTS

| | | | |
|---|---|---|---|
| 3,890,953 | 6/1975 | Kraus et al. | 128/82.1 |
| 4,157,299 | 6/1979 | Landowne | 210/658 |
| 4,257,771 | 3/1981 | Yee | 436/104 |
| 4,659,617 | 4/1987 | Fujil et al. | 428/221 |

FOREIGN PATENT DOCUMENTS 0174827 3/1986 European Pat. Off. .
2083825 3/1982 United Kingdom .

OTHER PUBLICATIONS

Patent Abstracts of Japan, vol. 7, No. 57 (P-181) [1202].
Patent Abstracts of Japan, vol. 6, No. 19 (C-90) [897].

*Primary Examiner*—Ivars Cintins
*Attorney, Agent, or Firm*—Birch, Stewart, Kolasch & Birch

[57] ABSTRACT

A cell separator which can separate cells, especially lymphocytes, with high selectivity and high efficiency without changing the cell population ratio of the cells. The cell separator comprises fibrous material containing fibers including hydroxyl apatite.

13 Claims, 2 Drawing Sheets

CELL SEPARATOR DEVICE

BACKGROUND OF THE INVENTION

I. Field of the Invention

The present invention relates to a cell separator which separates particular types of cells from other types of cells, and to a process of producing the same.

II. Description of Prior Art

For the purpose of clinical test, immunodiagnosis and immunotherapy, particular type of cells are often separated from a mixture containing various types of cells.

However, when T cells, B cells, K cells or NK cells are to be separated from lymphocytes, no methods by which the desired cells can be separated without changing the cell population are known.

Japanese Patent Disclosure (Kokai) Nos. 204454/82 and 140886/81 disclose a method for separating and recovering T cells using an organic high molecular compound. More particularly, T cells are separated by using a polymer or copolymer of ethylene, propylene, vinyl chloride, vinyl acetate, styrene, divinylbenzene, acrylonitrile, methyl methacrylate in the form of granules, having an acidic functional group such as a sulfonic group, a carboxyl group, a phosphonic group and a phenol group. However, by this method, the remaining monomer gives a cytotoxic effect to the cells. Further, since the average diameter of the granules are small, the column is likely to become clogged.

The method in which a crosslinked dextran, Sephadex 10 (tradename of Pharmacia) is used as a cell separator, is, also officially recognized. In this method, large and adhesive cells such as macrophage and accessory cells are separated off by the attachement to the crosslinked dextran, and T cells and B cells pass therethrough. However, in this method, non-adhesive accessory cells pass through the crosslinked dextran, while a type of T cells attach thereto, so that the T cell population cannot be obtained in a complete form.

A method in which Nylon wool is used as a cell separator is also officially recognized as a method for obtaining cells enriched with T cells. However, by this method, although T cells with comparatively high purity can be obtained, the cell population of T cells changes. Further, the separation ability and separation pattern varies depending on the particular lot of the Nylon wool, on the manner of unravelling the Nylon wool, on the manner of packing the Nylon wool and on the manner of washing the Nylon wool.

Thus, a cell separator which can separate cells with high selectivity and without changing the cell population is needed to be provided.

SUMMARY OF THE INVENTION

Accordingly, the object of the present invention is to provide a cell separator which can separate a particular type of cells with high selectivity and reproducibility, and without changing the cell population.

Another object of the present invention is to provide a process of producing the cell separator.

Still another object of the present invention is to provide a device for separating cells by which the separation of cells can be effected easily and with high selectivity and reproducibility.

This invention provides a fibrous cell separator comprising fibers containing hydroxyl apatite.

The fibrous cell separator can be produced according to the process of the present invention which comprises the steps of spinning an aqueous suspension containing hydroxyl apatite and a binder into fibers; and collecting the fibers on a moving surface to obtain the fibrous hydroxyl apatite.

The present invention further provide a device for separating cells comprising a column and the fibrous cell separator of the present invention therein.

The cell separator of the present invention is particularly effective for recovering T cells and for eliminating immunosuppressive cells such as suppressor T cells. By using the cell separator of the present invention, T cells can be recovered with high selectivity without changing the cell population. Further, since the cell separator of the present invention is effective for adhering immunosuppressive cells such as suppressor T cells, the cell separator is useful in immunotherapy.

BRIEF DESCRIPTION OF THE DRAWINGS

The present invention will become more fully understood from the detail description given hereinbelow and the accompanying drawings which are given by way of illustration only, and thus are not limitative of the present invention, and wherein.

DETAILED DESCRIPTION OF THE PREFERRED EMBODIMENTS

Figure 1:
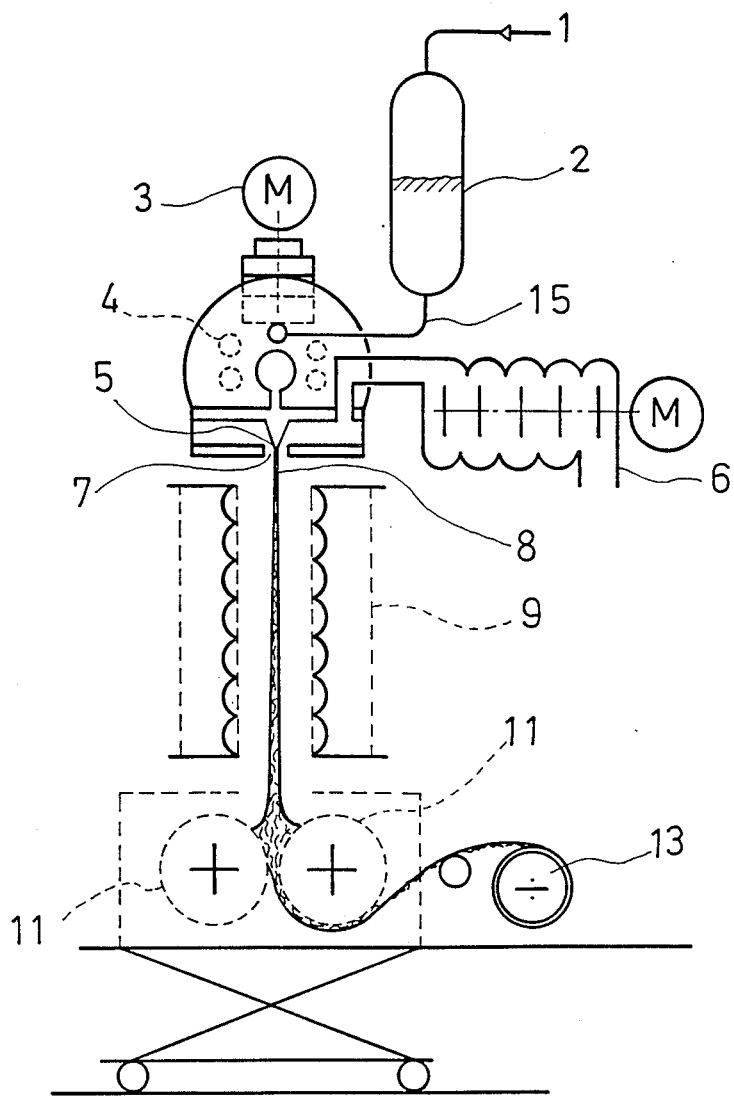
FIG. 1 shows a schematic view for explaining a process of producing the cell separator of the present invention.

As described above, the cell separator of the present invention comprises fibrous material containing fibers including hydroxyl apatite. The content of the hydroxyl apatite in the fiber is preferably 25% by weight, and more preferably 50% by weight. From the view point of the sensitivity of separation, it is preferred that the fibers constituting the fibrous material essentially consist of hydroxyl apatite. It should be noted, however, if the fiber essentially consists of hydroxyl apatite, the strength thereof is reduced. Thus, for increasing the strength of the fiber, a reinforcing material, such as, for example, calcium phosphate-based compound and water glass, may be incorporated in the fiber. Among the reinforcing materials, calcium phosphate-based compounds are preferred. The content of the reinforcing material in the fiber is usually 25% by weight or less. The cell separator may contain water. The water content in the cell separator is usually 50% by weight or less. The most preferred hydroxyl apatite is $Ca_5(PO_4)_3(OH)$ It is also preferred that the molar ratio of Ca/P is in the range of 1.4 to 1.8.

The diameter of the fiber constituting the cell separator of the present invention is not limited, but typically from 1 to 100 $\mu$m. The weight of the fibrous cell separator o the present invention is also not limited, but usually 5 g/m$^2$ to 500 g/m$^2$.

The fibrous cell separator of the present invention may be produced by a solution spinning process which utilizes a specific binder. The binder is preferred to be water-soluble. The organic macromolecules which satisfy this condition may preferably be used. Water-soluble linear macromolecules containing functional groups such as —OH, —COH, and —CONH$^2$ are preferred as the binder. Among the water-soluble macromolecules which may be used as the binder, preferred are polyvinyl alcohol, polycarboxymethyl cellulose, hydroxyethyl cellulose, hydroxypropyl cellulose, collagen, pullulan and chitin, polyacrylamide, polyacrylic acid, polymethacrylic acid, polyitaconic acid, polyethylene oxide, polyvinyl pyrrolidone, polyvinylmethylene ether, xanthine gum and guar gum. Among these, pullulan is most preferred. The molecular weight of the macromolecules may preferably be 20,000 to 2,000,000, and more preferably 50,000 to 1,000,000. These macromolecules may be used independently or in combination.

The hydroxyl apatite which is used as a starting material of the process may preferably be in the form of super fine particles. The super fine particles are preferably in the form of a rod, of which diameter is preferably 5 nm to 1 $\mu$m. Such hydroxyl apatite particles may be produced by a well-known conventional method. For example, they can be produced by adding an aqueous phosphoric acid solution to a basic solution (pH7-11) containing calcium ions.

In the process of producing the fibrous cell separator of the present invention, an aqueous suspension containing the above-described binder and hydroxyl apatite is used as the starting material. The aqueous suspension preferably contains 10-90% by weight, more preferably 50-70% by weight, and still more preferably 60-65% by weight of water; 5-70% by weight, more 15-20% by weight of hydroxyl apatite; and 5-40% by weight, more preferably 15-30% by weight, and still more preferably 20-25% by weight of the binder. If the hydroxyl apatite content is less than 5% by weight, the strength of the produced fibrous material is small, and if the hydroxyl apatite content is more than 70% by weight, the viscosity of the aqueous suspension becomes undesirably too high.

To increase the fluidity of the suspension to improve the dispersion of the hydroxyl apatite, a surface active agent of carbonic acid-based, plasticizer and/or softening agent such as polyols including glycerin, sorbitol, mannitol, ethylene glycol and polypropylene glycol may be added to the suspension, if desired. A defoaming agent may also be added. The content of such agents may typically be 0.01-5% by weight. When the above-described reinforcing material is used, the reinforcing material is dispersed in the suspension. It should be noted, however, when the reinforcing material is $Ca_3(PO_4)_2$, it can be formed in the sintering step as described later.

The aqueous suspension may be prepared under a temperature of about 20°-70° C.

An example of the process of producing the fibrous cell separator of the present invention, which utilizes the above-described aqueous suspension as the starting material will now be described referring to the accompanying drawing.

The aqueous suspension is supplied to a tank 2 through a supplying duct 1. The suspension is then supplied to a spinning nozzle 5, and is jetted from the nozzle by gear pumps 4 actuated by a motor 3. Air is supplied from a blower 6 to an air nozzle 7 which encircles the spinning nozzle 5, and is jetted from the air nozzle 7. The velocity of the air flow may be about 5 to about 1000 m/s, and the temperature of the air may be about 20° to 60° C. A plurality of the spinning and air nozzle assemblies may be provided, and the air nozzles may be disposed in a row, or in a circle. By the simultaneous jetting of the aqueous suspension and the air, the aqueous suspension is spun into a bundle of fine fibers 8. The diameter of the fibers may be adjusted by controlling the air velocity, to typically about 1 to 30 $\mu$m, and preferably about 1 to 10 $\mu$m. The higher the velocity of the air, the smaller the diameter of the fibers. When the air velocity is 1000 m/s, fibers of about 1 $\mu$m diameter are obtained. When the air velocity is 300 m/s and 30 m/s, fibers of about 3-5 $\mu$m diameter, and 20 $\mu$m diameter are obtained, respectively.

The thus formed bundle of fine fibers 8 is then heat-dried by a heater 9. The heater 9 may be, for example, an infrared heater, far infrared heater, or a microwave heater. The fibers are dried and solidified by the heater 9 to the water content of, for example, 10% by weight or less and preferably 7% by weight or less. If the drying is not sufficient, a fibrous material consisting of the fine fibers may not be obtained. The heating temperature varies depending on the amount of the material ejected from the spinning nozzle 5, on the temperature of the air jet, and on the amount of the air jet. Usually, the temperature of the heater 9 is in the range of about 200° to 500° C. (the temperature of the fibers being about 80° to 150° C.). If the heating temperature is too high, the binder may be decomposed.

The thus dried fibers are then collected on a moving collecting means 11 by dropping the fibers on the moving collecting means in an intercrossing manner to obtain a fibrous material. The collecting means 11 may be, for example, a wire net drum or a wire net belt. Two wire net drums rotating in the opposite direction may preferably be used. If the fibers are dropped on the contact portion of the two drums, a voluminous fibrous material in which the intercrossed fibers are three-dimensionally disposed, i.e., a fibrous material in the form of cotton or absorbent cotton, may be obtained. If the fibers are dropped on a portion other than the contact portion of the drums, a planar fibrous material in which the intercrossed fibers are arranged two-dimensionally, i.e., a fibrous material in the form of a non-woven fabric, may be obtained. The fibrous material in the form of a roving may be obtained by using a plurality of spinning nozzles disposed in a circle. By controlling the moving speed of the collecting means, fibrous material of 5 g/m$^2$ to 500 g/m$^2$ may be obtained. The thus formed fibrous material may be spooled on a reel 13.

It is preferred that the thus obtained fibrous material in which the fibers are bound each other by the binder be sintered to eliminate the binder. The sintering may be conducted under a temperature of about 350° to 1350° C., preferably about 400° to 1200° C., and more preferably about 650° to 1100° C. If the sintering is conducted under a temperature higher than 1350° C., the hydroxyl groups of the hydroxyl apatite may be decomposed to reduce the selectivity of the cell separator. If the sintering is conducted under a temperature of 1100° C. to 1300° C., $Ca_3(PO_4)_2$ is generated, so that the strength of the fibers may be improved.

The fibrous cell separator of the present invention may be modified by attaching thereto hyaluronic acid, chondroitin sulfate, chitin derivative, fibronectin, osteonectin or mucopolysaccharide or a derivative thereof to change the physicochemical properties and immunological properties of the surface of the hydroxyl apatite. By so doing, it may be possible to effectively change the separation characteristics of the cell separator to obtain a sharp elution pattern, or to control the separation spectrum. Further, particular sub-population of cells may be selectively collected.

Figure 2:
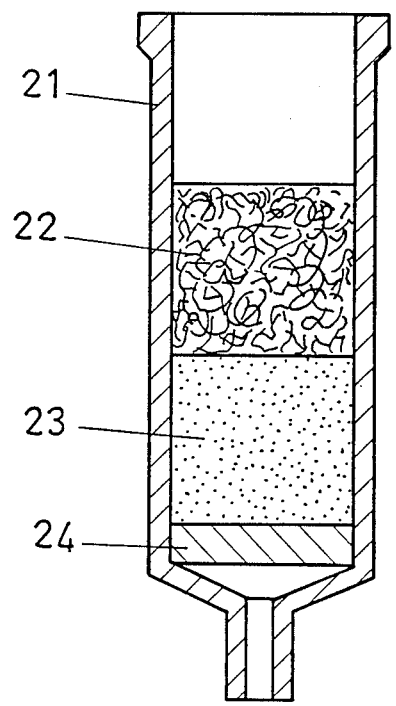
FIG. 2 shows a schematic cross-sectional view of an embodiment of the device for cell separation of the present invention.

A preferred embodiment of the device for separating cells utilizing the cell separator of the present invention will now be described referring to FIG. 2. The device comprises a column 21, and fibrous hydroxyl apatite 22 is contained therein. Separation of cells can be satisfactorily conducted by using the device with this simple structure. However, if hydroxyl apatite granules are used in combination with the fibrous hydroxyl apatite, the effectiveness of the cell separation is further promoted. Thus, in the embodiment shown in FIG. 2, hydroxyl apatite granules 23 are contained in the column 21 under the fibrous hydroxy apatite. The average diameter of the hydroxy apatite granules 23 is usually about 1 $\mu$m to 2000 $\mu$m, and preferably 50 $\mu$m to 2000 $\mu$m. It is preferred that the hydroxy apatite granules be sintered at a temperature of about 600° to 1350° C. It is also preferred that the molar ratio of Ca/P in the hydroxyl apatite is about 1.4 to 1.8. To prevent the escape of the granules 23 out of the column 21, a filter 24 is provided at a lower portion of the column under the hydroxyl apatite granules 23. The filter 24 may be a porous body or fibrous material of plastic, glass or ceramics which is conventionally used. The hydroxyl apatite granules may also be placed above the fibrous hydroxyl apatite 22.

Cell separation can be conducted by pouring a cell suspension or blood sample containing various types of cells from the top of the column.

By using the above-mentioned device of the present invention, cells may be separated without immunologically stimulating them, with high sensitivity. The separation operation is very simple, and the time required for cell separation may be reduced to as short as one tenth of that required in the conventional methods. T cells may be collected by using the device of the present invention, which is substantially free from contaminated macrophages. Further, the contamination of monocyte may also be kept very small.

Further, the device of the present invention may be used for removing immunosuppressive cells such as suppressor T cells, so that immunotherapy can be conducted using the device. By removing the immunosuppressive cells from the body, the immunological power of the patient may be recovered. The removal of the immunosuppressive cells may be possible by directly connecting the device to a bloodvessel via a flexible tube, as described in the examples later described.

Preferred examples of the present invention will now be described. The examples are presented for the illustration purpose only, and should not be interpreted restrictively.

EXAMPLE 1

An aqueous suspension containing 9% by weight of pullulan powder of which average molecular weight is 200,000, 42% by weight of hydroxyl apatite powder (particles of 5 to 80 nm diameter), 1% by weight of dispersant (carbonic acid-based surface active agent), and 48% by weight of water were vigorously stirred under the room temperature to uniformly disperse the pullulan in the aqueous system. The aqueous suspension was then defoamed. Using this suspension as the starting material, and using the apparatus shown in FIG. 1, fibrous hydroxyl apatite (Ca/P ratio of 1.66) of which fibers have an average diameter of 10 to 15 $\mu$m was produced. The fibrous hydroxyl apatite was then sintered at 1100° C.

In a column with inner volume of 10 ml, 0.02 g of glass wool was packed such that the packed glass wool has a volume of 0.8 ml. On the glass wool filter, 0.7 g of fibrous hydroxyl apatite obtained as above was packed in a volume of 1.5 ml to obtain a device for cell separation.

The column was washed firstly with physiological saline, then with a culture medium RPMI-1640 at 37° C., and finally with RPMI-1640 containing 10% by weight of fetal calf serum.

Lymphocytes were previously separated from normal human peripheral blood by a conventional Ficoll-Isopaque specific gravity centrifugation method. The cells were then suspended on RPMI-1640 medium containing 10% by weight of fetal calf serum at a population density of $1 \times 10^8$ cells/ml. A 0.4 ml aliquote thereof was placed on the top of the column to permeate the liquid into the fibrous hydroxyl apatite, and the column was then incubated at 37° C. for 1 hour. Thereafter, the cells were eluted with RPMI-1640 medium.

The cell population before and after passing through the column was counted using a hemocytometer. The recovery was 58%.

EXAMPLE 2

In a column with inner volume of 5 ml, 0.02 g of glass wool was packed such that the packed glass wool has a volume of 08. ml. On the glass wool filter, 0.2 g of fibrous hydroxyl apatite of which average diameter is 5 to 10 $\mu$m (Ca/P ratio of 1.66) which was sintered at 1000° C. was packed in a volume of 0.4 ml to obtain a device for cell separation as shown in FIG. 2.

The same operation was conducted as in Example 1 to obtain a recovery of cells of 82%.

EXAMPLE 3

In a column with inner volume of 5 ml, 0.02 g of glass wool was packed such that the packed glass wool has a volume of 0.8 ml. On the glass wool filter, 0.15 g of fibrous hydroxyl apatite of which average diameter is 5 to 10 $\mu$m (Ca/P ratio of 1.66) produced as in Example 1 was packed to the volume of 0.5 ml to obtain a device for cell separation.

The same operation was conducted as in Example 1 to obtain a recovery of cells of 74%.

EXAMPLE 4

In a column with inner volume of 5 ml, 0.02 g of glass wool was packed to a volume of 0.8 ml. On the glass wool filter, 0.35 g of hydroxyl apatite granules with an average diameter of 400 to 500 $\mu$m (Ca/P ratio of 1.67) which were sintered at 700° C. was packed in a volume of 0.4 ml. On the hydroxyl apatite granules, 0.15 g of fibrous hydroxyl apatite of which average diameter is 5 to 10 $\mu$m (Ca/P ratio of 1.66) which was sintered at 1000° C. was packed in a volume of 0.4 ml to obtain a device for cell separation as shown in FIG. 2.

The same operation was conducted as in Example 1 to obtain a recovery of cells of 80%.

EXAMPLE 5

In a column with inner volume of 5 ml, 0.02 g of glass wool was packed to a volume of 0.8 ml. On the glass wool filter, 0.35 g of hydroxyl apatite granules with an average diameter of 400 to 500 $\mu$m (Ca/P ratio of 1.67) which were sintered at 700° C. was packed in a volume of 0.4 ml. On the hydroxyl apatite granules, 0.1 g of fibrous hydroxyl apatite of which average diameter is 5 to 10 μm (Ca/P ratio of 1.66) which was sintered at 1000° C. was packed in a volume of 0.4 ml to obtain a device for cell separation as shown in FIG. 2.

The same operation was conducted as in Example 1 to obtain a recovery of cells of 84%.

COMPARATIVE EXAMPLE 1

In a column of 5 ml of inner volume, 0.02 g of glass wool was packed in a volume of 0.8 ml, and then 0.8 g of hydroxyl apatite granules of an average diameter of 400 to 500 μm (Ca/P ratio of 1.67) which was sintered at 700° C. was packed in 0.8 ml volume to prepare a device for cell separation.

COMPARATIVE EXAMPLE 2

The same device as in Example 1, except that Nylon wool was used in place of hydroxyl apatite granules was prepared.

TEST

Using the devices for cell separation of Examples 1 to 5 and Comparative Examples 1 and 2, T cells, B cells and monocytes in the eluted liquid after passing through the column were counted. The counting was conducted by a conventional method by labelling the cells with fluorescence-labelled antibodies Leu 1, Leu 12 or Leu $M^3$, (commercially available from Fujisawa Pharmaceutical Co., Ltd., Osaka, Japan) and using a fluorescence activated cell sorter. The results are shown in Table 1. In Table 1, percentages of each type of cells in the cell population are shown.

TABLE 1

| Example | Recovery (%) | T cells (Leu 1) | B cells (Leu 12) | Monocytes (Leu $M_3$) |
|---|---|---|---|---|
| 1 | 75 | 97 | 1.3 | 0.8 |
| 2 | 82 | 95 | 1.0 | 0.5 |
| 3 | 74 | 96 | 1.1 | 1.1 |
| 4 | 80 | 97 | 0.8 | 0.8 |
| 5 | 84 | 95 | 2.7 | 0.8 |
| Comp. Ex. 1 | 85 | 94 | 3.5 | 2.3 |
| Comp. Ex. 2 | 37 | 90 | 5.0 | 4.8 |

As shown in Table 1, in the examples of the present invention, the percentage of the contaminated B cells and monocytes were significantly smaller than those obtained in the comparative examples. Thus, it is clear that the cell separator of the present invention has a higher selectivity than the conventional cell separators.

EXAMPLES 6-8

In a tuberculin syringe of 1 ml inner volume, 0.02 g of glass wool was packed in a volume of 0.02 ml. On the glass wool filter, 0.4 g/0.4 ml of hydroxyl apatite granules of 400 to 600 μm diameter and 0.1 g/0.4 ml of fibrous hydroxyl apatite (5 to 20 μm diameter) were packed in the order mentioned to prepare a device for cell separation as shown in FIG. 2.

From normal human peripheral blood, lymphocytes were separated by Ficoll-Isopaque specific gravity centrifugation method, and $2-10^7$ cells were suspended in 0.2 ml of RPMI-1640 medium containing 10% by weight of fetal calf serum.

The cell suspension was placed on the top of the column and was permeated into the filler. Thereafter, 5 ml of RPMI-1640 was passed through the syringe to elute the cells. The eluted cell population was counted conducting two-color staining using fluorescence-labelled antibodies Leu 2 and Leu 15 (commercially available from Fujisawa Pharmaceuticals Co., Ltd., Osaka, Japan) and a fluorescence activated cell sorter.

EXAMPLE 9

The same procedure as in Examples 6-8 was repeated except that the sample lymphocytes were prepared from peripheral blood of a patient suffering from acoustic neuroma.

EXAMPLE 10

The same procedure as in Examples 6-8 was repeated except that the sample lymphocytes were prepared from peripheral blood of a patient suffering from upper jaw cancer.

EXAMPLE 11

The same procedure as in Examples 6-8 was repeated except that the sample lymphocytes were prepared from peripheral blood of a patient suffering from colon cancer.

EXAMPLE 12

Peripheral blood (containing heparin) from a normal human was diluted two-fold with physiological saline, and 5 ml aliquote thereof was passed through the syringe as in Examples 6-7. Thereafter, red blood cells were lysed with ammonium chloride solution in Tris buffer to separate lymphocytes, and then the cell population of the lymphocytes was determined as in Examples 6-8.

TEST RESULTS

The percentages of the immunosuppressive cells in the cell population before and after passing the column were shown in Table 2.

TABLE 2

| Examples | Before Passing (%) | After Passing (%) |
|---|---|---|
| 6 | 1.33 | 0.77 |
| 7 | 5.12 | 1.26 |
| 8 | 1.41 | 0.54 |
| 9 | 15.05 | 0.18 |
| 10 | 1.91 | 0.81 |
| 11 | 7.97 | 2.73 |
| 12 | 7.49 | 0.26 |

It is apparent from Table 2 that significant part of the immunosuppressive cells were removed by passing the lymphocytes through the device of cell separation of the present invention.

EXAMPLE 13

To ten rats of 8 weeks old, Walker 256 cells (a cancer cell of rats) were transferred. After 3 days from the transfer, blood was collected from a vein in the right femoral region of the rats and was returned to a vein in the left femoral region after passing through the syringe prepared as in Examples 6-8. This circulation was continued for 1 hour. In this operation, heparin was used for preventing the blood from clogging. After 4 days from the circulation, delayed footpad reaction tests were conducted using sheep red blood cells. Further, the survival duration of the rats were also checked. The results are shown in Table 3.

TABLE 3

| | Immune Function | Survival Days |
|---|---|---|
| Experimental Group | Normal | 22 days |
| Control Group | Weakened | 15 days |

As is apparent from Table 3, by conducting the circulation through the cell separating device of the present invention, the immune function was kept normal and the survival days were extended 1.5 times. Thus, the device for cell separation of the present invention is also effective for removing immunosuppressive cells.

We claim:

1. A device for separating cells with high selectivity and reproducibility and without substantially changing the cell population, which comprises:

a separating column;

fibers containing hydroxyl apatite disposed in said separating column;

inlet means for introducing cells to be separated into said separating column; and outlet means for removing cells from said separating column.

2. The device of claim 1 wherein the content of the hydroxyl apatite in the fiber is 25 to 50% by weight.

3. The device of claim 1 wherein a reinforcing material is incorporated into the fiber.

4. The device of claim 3 wherein the reinforcing material is calcium phosphate and water glass which is present in an amount of up to 25% by weight.

5. The device of claim 1 wherein the cell separator contains water in an amount of up to 50% by weight.

6. The device of claim 1 wherein the hydroxyl apatite is $Ca_5(PO_4)_3(OH)$ in which the molar ratio of Ca/P is 1.4 to 1.8.

7. The device of claim 1 wherein the diameter of the fiber is 1 to 100 $\mu m$.

8. The device of claim 1 wherein the weight of the fibrous cell separator is 5 $g/m^2$ to 500 $g/m^2$.

9. The device of claim 1 wherein the column further contains granules of hydroxly apatite.

10. A device for separating cells with high selectivity and reproducibility and without substantially changing the cells population which comprises a column, inlet means for introducing cells to be separated into said column; outlet means for removing cells from said column, a filter disposed at the lower portion of the column, and fibers containing hydroxyl apatite disposed on said filter.

11. The device of claim 10 wherein hydroxyl apatite granules are placed on the filter and under the fibrous bydroxyl apatite.

12. The device of claim 11 wherein the average diameter of the hydroxyl apatite granules is 1 to 2000 $\mu m$.

13. The device of claim 11 wherein the granules are sintered at a temperature of 500° to 1,4000° C.

* * * * *